United States Patent
Nagar et al.

(10) Patent No.: US 11,430,281 B1
(45) Date of Patent: Aug. 30, 2022

(54) DETECTING CONTAMINATION PROPAGATION

(71) Applicant: INTERNATIONAL BUSINESS MACHINES CORPORATION, Armonk, NY (US)

(72) Inventors: Raghuveer Prasad Nagar, Kota (IN); Sarbajit K. Rakshit, Kolkata (IN); Amitava Kundu, Bangalore (IN); Rajasekhar Thallam, Bangalore (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 17/222,682

(22) Filed: Apr. 5, 2021

(51) Int. Cl.
*G07C 9/37* (2020.01)
*G06N 20/00* (2019.01)
*G06T 7/00* (2017.01)
*A61B 5/00* (2006.01)
*A61B 90/00* (2016.01)

(52) U.S. Cl.
CPC ............ *G07C 9/37* (2020.01); *G06N 20/00* (2019.01); *G06T 7/0012* (2013.01); *A61B 5/00* (2013.01); *A61B 5/0079* (2013.01); *A61B 2090/081* (2016.02); *G06T 7/00* (2013.01)

(58) Field of Classification Search
CPC .... G06N 20/00; G07C 9/37; A61B 2090/081; A61B 5/0079; G06T 7/0012
See application file for complete search history.

(56) References Cited

U.S. PATENT DOCUMENTS

| | | | | |
|---|---|---|---|---|
| 10,052,026 | B1* | 8/2018 | Tran | A61B 5/165 |
| 2017/0109484 | A1* | 4/2017 | Herger | G06T 7/70 |
| 2017/0200009 | A1* | 7/2017 | Bertolet | G06F 9/4406 |
| 2017/0319148 | A1* | 11/2017 | Shahin | A61B 5/02055 |
| 2018/0343418 | A1* | 11/2018 | Van Ness | H04N 7/147 |
| 2019/0130652 | A1* | 5/2019 | Yu | G06T 19/006 |

(Continued)

OTHER PUBLICATIONS

R. Miotto et al., "Reflecting Health: Smart Mirrors for Personalized Medicine", npj Digital Medicine; 10.1038/s41746-018-0068-7; Nov. 8, 2018, Total 7 pp.

(Continued)

*Primary Examiner* — Thomas D Alunkal
(74) *Attorney, Agent, or Firm* — Konrad, Raynes, Davda & Victor LLP; Janaki K. Davda

(57) ABSTRACT

Provided are techniques for detecting contamination propagation and performing decontamination. In response to receiving a request to detect contaminants and perform decontamination, an entity is identified. Whether there are contaminants on the entity is detected using any combination of sensor data, one or more images, and one or more contamination propagation patterns. In response to determining that there are no contaminants, the entity is allowed to pass through an entry point. In response to determining that there are contaminants, one or more decontamination techniques are identified, decontamination of the entity is performed, using the one or more decontamination techniques, and, in response to determining that the decontamination has been successful, the entity is allowed to pass through the entry point.

20 Claims, 11 Drawing Sheets

(56) References Cited

U.S. PATENT DOCUMENTS

2020/0397546 A1* 12/2020 Miller ............... A46B 15/0026
2021/0132795 A1* 5/2021 Kurbanova ......... G06F 3/04886

OTHER PUBLICATIONS

H. S. Maghdid et al., "A Novel AI-enabled Framework to Diagnose Coronavirus COVID-19 using Smartphone Embedded Sensors: Design Study", Human-Computer Interaction; Machine Learning; Populations and Evolution; arXiv:2003.07434; May 30, 2020, Total 5 pp.

N. I. Khan, "System and Method of Smart Mirror to Detect Anomaly in Fashion Accessory and Identify Health Symptoms", IP.com Prior Art Database; IPCOM000263513D; Sep. 5, 2020, Total 5 pp.

"E-textiles", Wikipedia, [online][retrieved Apr. 2, 2021], https://en.wikipedia.org/wiki/E-textiles, Total 7 pp.

"Transmission (medicine)", Wikipedia, [online][retrieved Mar. 9, 2021], https://en.wikipedia.org/wiki/Transmission_(medicine), Total 11 pp.

"The Magic of Smart Mirrors: Artificial Intelligence, Augmented Reality and the Internet of Things", Oct. 4, 2019, [online][retrieved Mar. 9, 2021], https://www.forbes.com/sites/bernardmarr/2019/10/04/the-magic-of-smart-mirrors-artificial-intelligence-augmented-reality-and-the-internet-of-things/?sh=427065da615b, Total 5 pp.

"Smart Mirror | IIT School of Applied Technology", 2016, [online][retrieved—Mar. 9, 2021], https://appliedtech.iit.edu/smart-lab-information-technology-and-management/projects/smart-mirror. Total 5 pp.

"Simulating city-level airborne infectious diseases", ScienceDirect, May 2015, [online][retrieved—Mar. 9, 2021], https://www.sciencedirect.com/science/article/pii/S0198971514001367, Total 25 pp.

Mell, P. et al., "Effectively and Securely Using the Cloud Computing Paradigm", [online], Oct. 7, 2009, retrieved from the Internet at <URL: http://csrc.nist.gov/groups/SNS/cloud-computing/cloud-computing-v26.ppt>, Total 80 pp.

Mell, P. et al., "The NIST Definition of Cloud Computing (Draft)", Sep. 2011, Computer Security Division Information Technology Laboratory National Institute of Standards and Technology, Total 7 pp.

"Radioactive Contamination and Radioactive Exposure", Centers for Disease Control and Prevention, [online][retrieved Apr. 5, 2021] https://www.cdc.gov/nceh/radiation/emergencies/contamination.html, Total 2 pp.

"Predicting hospital infections: how AI makes it possible", Wolters Kluwer, Mar. 1, 2019, [online][retrieved—Apr. 5, 2021] https://www.wolterskluwer.com/en/expert-insights/predicting-hospital-infections-how-ai-makes-it-possible, Total 7 pp.

"Forecasting Infectious Disease Spread with Web Data", LiveScience.com, Dec. 10, 2014, [online][retrieved—Apr. 5, 2021] https://www.livescience.com/49019-web-data-helps-forecast-infectious-diseases.html, Total 15 pp.

C.D. Corley, et al., "Disease Prediction Models and Operational Readiness", Mar. 19, 2014, [online][retrieved—Apr. 5, 2021] https://journals.plos.org/plosone/article?id=10.1371/journal.pone.0091989, Total 13 pp.

"Calling in Sick with a Case of the Mondays", germtrax Health and Wellness, Jul. 6, 2012, [online] [retrieved—Apr. 5, 2021] https://germtrax.com/, Total 14 pp.

"Cell Culture Contamination Detection Kit", ThermoFisher Schientific, [online][retrieved—Apr. 5, 2021] https://www.thermofisher.com/order/catalog/product/C7028#/C7028, Total 3 pp.

"Hospital-acquired Infections", Philips, [online][retrieved—Apr. 5, 2021] https://www.philips.nl/c-dam/b2bhc/master/whitepapers/hospital-acquired-infections/HAI_supplies_slip_sheet.pdf, Total 2 pp.

"Contamination of equipment in emergency settings: An exploratory study with a targeted automated intervention", ncbi.nlm.nih.gov, Jul. 30, 2009, [online][retrieved—Apr. 5, 2021] https://www.ncbi.nlm.nih.gov/pmc/articles/PMC2731103/, Total 16 pp.

"HAI Prevention Technology", infectioncontroltoday.com, [online][retrieved—Apr. 5, 2021] https://www.infectioncontroltoday.com/view/hai-prevention-technology, Total 14 pp.

P. Vanhems, et al., "Estimating Potential Infection Transmission Routes in Hospital Wards Using Wearable Proximity Sensors", journals.plos.org, Sep. 11, 2013, [online][retrieved—Apr. 5, 2021] https://journals.plos.org/plosone/article?id=10.1371/journal.pone.0073970, Total 11 pp.

* cited by examiner

DETECTING CONTAMINATION PROPAGATION

BACKGROUND

Embodiments of the invention relate to detecting contamination propagation. In addition, embodiments of the invention relate to performing decontamination using a smart mirror.

A contaminant may be described as something that makes a surface or a substance unclean or no longer suitable for use. For example, germs may be considered contaminants. The surface may be a floor, a bed, a wall, clothing, hair, skin, etc. The substance may be body fluids, water, air, food, etc.

Maintaining hygiene is a factor in having a clean (i.e., contaminant-free or mostly contaminant-free) surface and substance. Contamination may spread due to various factors, such as with wind flow direction and with cross contamination. In many cases, there may be one or more entry points through which the contamination may spread in a surrounding area.

People who are externally contaminated (e.g., with germs on hands or on clothing) may spread the contaminant by touching surfaces, sitting in a chair or even walking through a house. Contaminant may fall from clothing and contaminate other surfaces.

Areas (e.g., homes) may also become contaminated with contaminants (e.g., radioactive materials) in body fluids from internally contaminated people.

SUMMARY

In accordance with certain embodiments, a computer-implemented method is provided for detecting contamination propagation and performing decontamination using a smart mirror. The computer-implemented method comprises operations. In response to receiving a request to detect contaminants and perform decontamination, an entity is identified. Whether there are contaminants on the entity is detected using any combination of sensor data, one or more images, and one or more contamination propagation patterns. In response to determining that there are no contaminants, the entity is allowed to pass through an entry point. In response to determining that there are contaminants, one or more decontamination techniques are identified, decontamination of the entity is performed, using the one or more decontamination techniques, and, in response to determining that the decontamination has been successful, the entity is allowed to pass through the entry point.

In accordance with other embodiments, a computer program product is provided for detecting contamination propagation and performing decontamination using a smart mirror. The computer program product comprises a computer readable storage medium having program code embodied therewith, the program code executable by at least one processor to perform operations. In response to receiving a request to detect contaminants and perform decontamination, an entity is identified. Whether there are contaminants on the entity is detected using any combination of sensor data, one or more images, and one or more contamination propagation patterns. In response to determining that there are no contaminants, the entity is allowed to pass through an entry point. In response to determining that there are contaminants, one or more decontamination techniques are identified, decontamination of the entity is performed, using the one or more decontamination techniques, and, in response to determining that the decontamination has been successful, the entity is allowed to pass through the entry point.

In accordance with yet other embodiments, a computer system is provided for detecting contamination propagation and performing decontamination using a smart mirror. The computer system comprises one or more processors, one or more computer-readable memories and one or more computer-readable, tangible storage devices; and program instructions, stored on at least one of the one or more computer-readable, tangible storage devices for execution by at least one of the one or more processors via at least one of the one or more memories, to perform operations. In response to receiving a request to detect contaminants and perform decontamination, an entity is identified. Whether there are contaminants on the entity is detected using any combination of sensor data, one or more images, and one or more contamination propagation patterns. In response to determining that there are no contaminants, the entity is allowed to pass through an entry point. In response to determining that there are contaminants, one or more decontamination techniques are identified, decontamination of the entity is performed, using the one or more decontamination techniques, and, in response to determining that the decontamination has been successful, the entity is allowed to pass through the entry point.

BRIEF DESCRIPTION OF THE SEVERAL VIEWS OF THE DRAWINGS

Referring now to the drawings in which like reference numbers represent corresponding parts throughout.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Embodiments determine the propagation pattern of contaminants ("contamination propagation pattern") to detect contamination propagation. Then, embodiments perform decontamination of entities (e.g., people and objects). This prevents the spread of contaminants by the entity. For example, such decontamination of the entity with contaminants (e.g., contaminated surfaces or body fluids) prevents other from coming into contact with the contaminants in an area (e.g., a home, a hospital, etc.).

Figure 1:
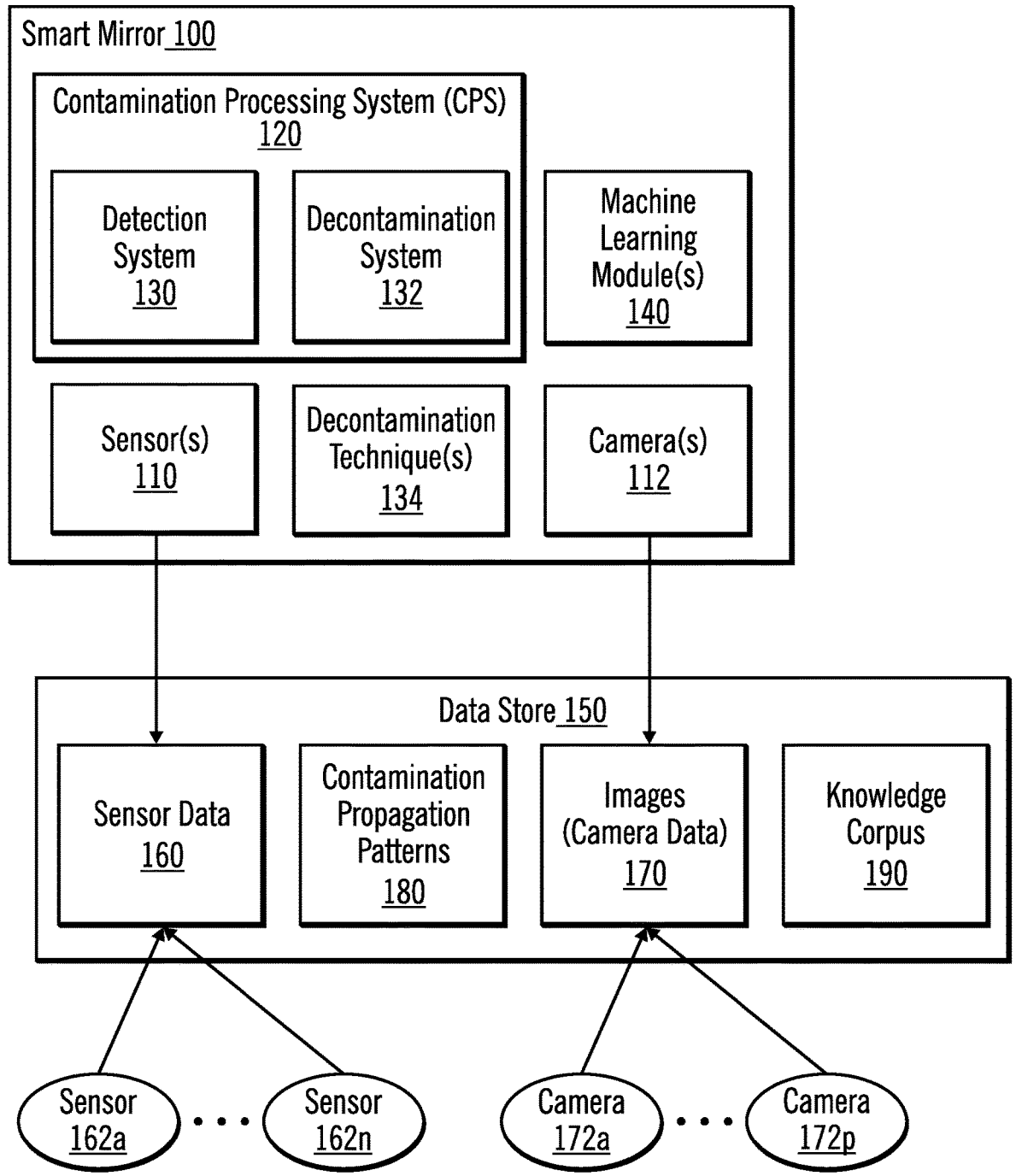
FIG. 1 illustrates, in a block diagram, a computing environment of a smart mirror in accordance with certain embodiments.

FIG. 1 illustrates, in a block diagram, a computing environment of a smart mirror 100 in accordance with certain embodiments. The smart mirror 100 includes a Contamination Processing System (CPS) 120 and one or more machine learning modules 140. The Contamination Processing System (CPS) 120 includes a detection system 130 and a decontamination system 132. In certain embodiments, although illustrated as two components, the functionality of the detection system 130 and the decontamination system 132 are in one component.

The detection system 130 determines whether an entity is contaminated. If so, the decontamination system 132 attempts to decontaminate (i.e., remove the contaminants or neutralize/minimize the contaminants so that they do not cause harm) using one or more decontamination techniques 134. In certain embodiments, the decontamination techniques 134 kill germs. If the decontamination does not work, then the smart mirror denies entry to the entity (e.g., the entity cannot leave a hospital or cannot enter a patient room). A machine learning module 140 may be used by the detection system 130 to determine whether the entity is contaminated. Another machine learning module 140 may be used by the decontamination system 132 to select one or more decontamination techniques 134.

The smart mirror 100 includes one or more sensors 110 and one or more cameras 112. The cameras 112 may take images of the entity. For example, if the image is of a doctor, the smart mirror 100 may check for contamination differently than for an object, such as a stethoscope.

The smart mirror 100 is connected to a data store 150. The data store 150 stores sensor data 160 from the sensors 110 and sensors 162a . . . 162n (where there may be one or more sensors 162a . . . 162n). The sensors 162a . . . 162n may be part of smart attire or part of wearable devices (e.g., a smart watch). The smart attire may also be referred to as "electronic cloth-based dress" or "electronic dress". Smart attire includes clothing, shoes, and accessories (e.g., gloves, face shields, headbands, wrist bands, etc.) made with electronic textiles ("e-textiles"). The smart attire may be described as any item made from electronic textiles that a user may wear (e.g., a top, pants, a jacket, shoes, socks, etc.) or carry (e.g., a blanket, a towel, etc.). For entities that are objects (e.g., a stethoscope), the smart attire may be an electronic textile that is used to cover or wrap the object.

The sensors 162a . . . 162n may include location sensors that provide location data (e.g., latitude and longitude coordinates (x,y)) to the smart mirror 100. The location data may be used to determine a path of an entity through an area (e.g., a building, a park, etc.). The sensor data 160 may include health parameters of an entity wearing the smart attire (e.g., pulse rate, temperature, muscle stretch, heart rhythm, physical movement, etc.). The data store 150 stores camera data 170 with images from the camera 112 and cameras 172a . . . 172p (where there may be one or more cameras 172a . . . 172p).

The data store 150 also stores contamination propagation patterns 180 and a knowledge corpus 190. A contamination propagation pattern 180 may be described as a path that a contaminated entity takes (e.g., a doctor entered a lab, then visited a patient in a room, and stopped by a nurse station) or may be described as a path that contaminants take (e.g., the doctor touched a first portion of a top with a contaminated right hand, touched the first portion of the top with the left hand, and touched a second portion of the top with the left hand, which results in contaminants moving from the first hand, to first portion, to left hand, to second portion). The knowledge corpus 190 may store historical data of types of touches on smart attire and, for each of the types of touches, a level of contamination and an associated confidence level. In certain embodiments, the data store 190 also stores the contaminants for each of the types of touches. Moreover, the data store 190 stores historical learning (e.g., rules indicating what was learned, such as touching an entity for 20 minutes is likely to result in high contamination with a confidence level of 75%.

In certain embodiments, the smart mirror 100 is provided at entry points. The entry points may be entrances (e.g., into a building or room) or exits (e.g., out of a building or room). The smart mirror 100 proactively detects and addresses the contamination.

In certain embodiments, the smart mirror 100 controls contamination propagation by detecting a contamination propagation pattern and, using that, detecting contamination at an entry point. Different types of contaminants may propagate in different manners, such as with contamination by air, cross contamination, etc. The smart mirror 100 analyzes the contamination propagation pattern and detects the points of the contamination (e.g., a particular room or area of a hospital), and, accordingly, addresses the contamination at the detected entry point.

In certain embodiments, the smart mirror 100 is part of an Internet of Things (IoT) and is machine learning based to detect and highlight contaminated areas of entities (e.g., body parts and smart attire) and to decontaminate the detected contaminated area.

The Internet of Things (IoT) may be described as a group of devices that are connected to the Internet and communicate with each other and/or the rest of the internet. Each of the devices typically has one or more sensors and/or one or more cameras to enable that device to collect sensor data and/or images and communicate the sensor data and/or images with other devices. The device is able to store the sensor data and the images and forward the sensor data and the images to another device.

In certain embodiments, the smart mirror 100 provides entity access management based on dynamic detection of contamination level at entry points. The entity is restricted on contamination detection and allowed on decontamination.

Figure 2A:
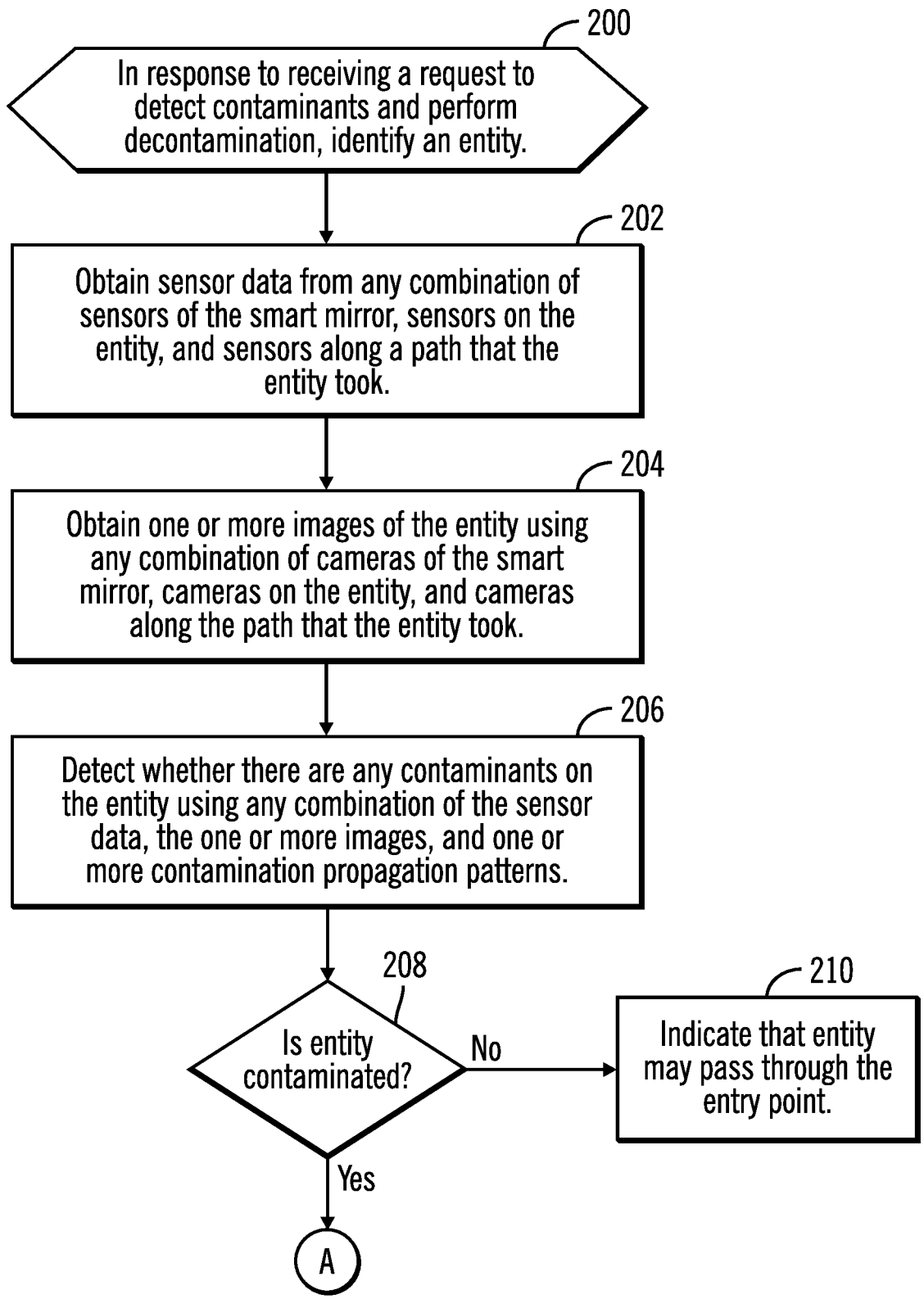
FIGS. 2A, 2B, and 2C illustrate, in a flowchart, operations for detecting contaminants and performing decontamination in accordance with certain embodiments.
Figure 2B:
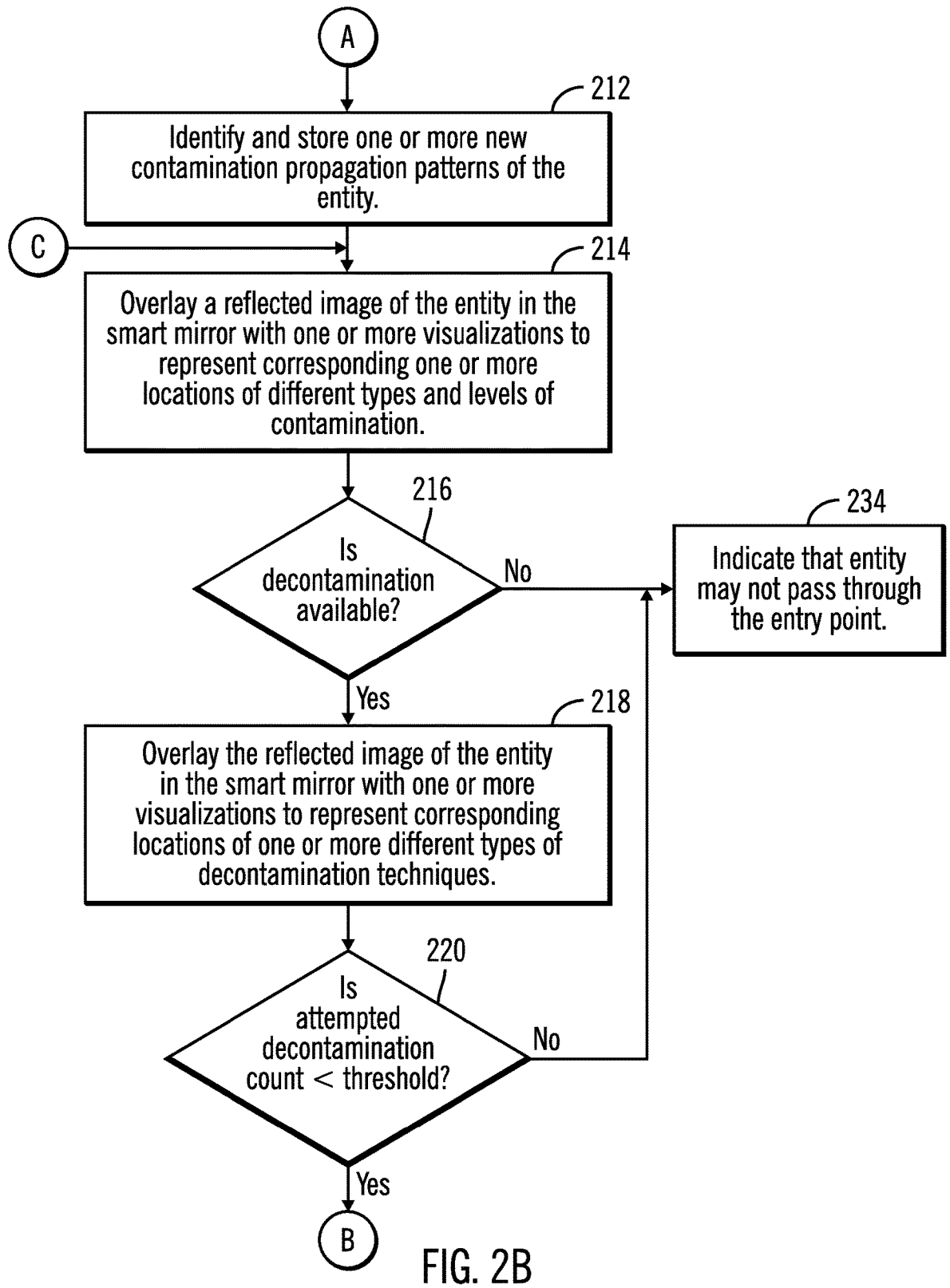
Figure 2C:
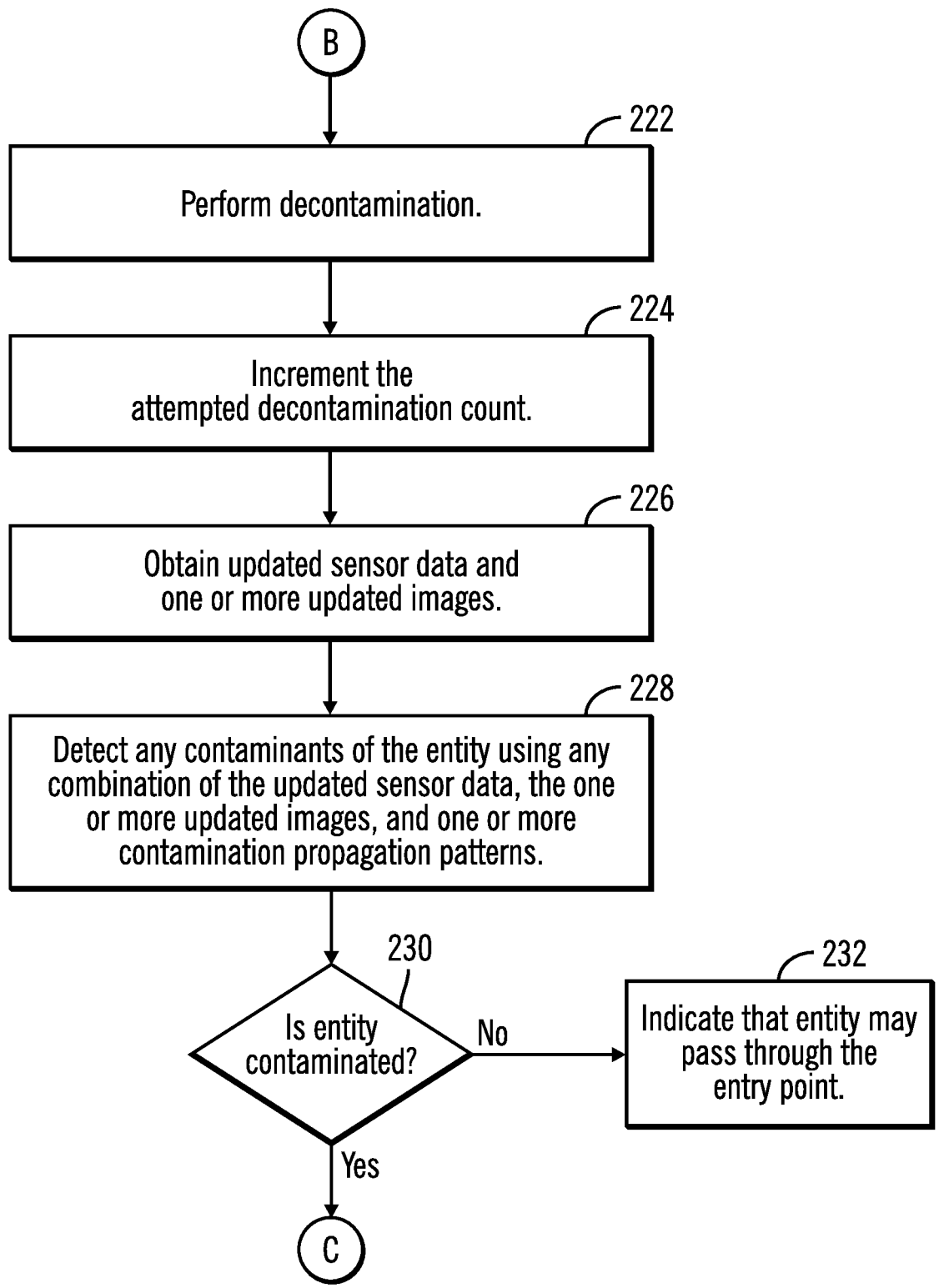

FIGS. 2A, 2B, and 2C illustrate, in a flowchart, operations for detecting contaminants and performing decontamination in accordance with certain embodiments. In response to receiving a request to detect contaminants and perform decontamination, control begins at block 200 with the detection system 130 identifying an entity standing in front of the smart mirror, which is by an entry point. For example, an entity who is a user may opt in for detection and decontamination by standing in front of the smart mirror 100 and 1) issuing a verbal request (e.g., "check for contamination" or "start decontamination"), 2) using a gesture (e.g., waving a hand in a certain way), 3) touching a portion of the mirror (e.g., lower right corner), etc. As another example, if the entity is an object, then a user may opt in for detection and decontamination by placing the object in front of the smart mirror 100 and 1) issuing a verbal request (e.g., "check for contamination" or "start decontamination"), 2) using a gesture (e.g., waving a hand in a certain way), 3) touching a portion of the mirror (e.g., lower right corner), etc.

In block 202, the detection system 130 obtains sensor data from any combination of sensors of the smart mirror, sensors on the entity (e.g., on smart attire or from smart devices), and sensors along a path that the entity took (e.g., sensors on a wall or floor). In block 204, the detection system 130 obtains one or more images of the entity using any combination of cameras of the smart mirror, cameras on the entity (e.g., on a watch worn by the entity), and cameras along the path that the entity took (e.g., cameras on a wall).

In block 206, the detection system 130 detects whether there are any contaminants on the entity by using any combination of the sensor data, the one or more images, and one or more contamination propagation patterns. In block 208, the detection system 130 determines whether the entity is contaminated. If so, processing continues to block 212 (FIG. 2B), otherwise, processing continues to block 210. In block 210, the detection system 130 indicates that the entity may pass through the entry point (i.e., access is allowed due to no contamination or a very low level (safe level) of contamination).

In block 212, the detection system 130 identifies and stores one or more new contamination propagation patterns of the entity (e.g., based on the path the entity took to the smart mirror 100 and/or based on the pattern of contaminants on the entity). The path may be determined using the sensor data and the images.

In block 214, the detection system 130 overlays the reflected image of the entity in the smart mirror with one or more visualizations to represent corresponding one or more locations of different types and levels of contamination. With embodiments, one or more contaminants may be visualized. For example, the visualization over the hand may indicate flu germs, while the visualization over a portion of the smart attire may indicate blood.

In certain embodiments, if the user is contaminated and stands in front of the smart mirror 100, then the detection system 130 highlights the areas on the body/dress that are contaminated so that the user may apply appropriate decontamination techniques.

For example, if the user is a doctor who has touched a patient to apply a treatment, the doctor becomes contaminated. Then, if the doctor stands in front of the smart mirror 100, then the smart mirror 100 highlights the areas on the doctor's reflection that are contaminated and should be decontaminated. Without the decontamination, the detection system 130 does not allow the doctor to pass through an entry point (e.g., the doctor is not allowed to leave the hospital until decontamination is completed).

In certain embodiments, an smart attire is paired with the smart mirror 100. Then, the detection system 130 identifies the contaminated area and overlays visual indicators on the reflected image of the smart mirror 100. This will help the user to understand which areas are contaminated on the user's smart attire or body.

The detection system 130 of the CPS system 120 passes control to the decontamination system 132 of the CPS system 120.

In block 216, the decontamination system 132 determines whether decontamination is available. If so, processing continues to block 218, otherwise, processing continues to block 234. If decontamination is not available, the detection system 130 of the CPS system 120 receives control back from the decontamination system 132 of the CPS system 120. In block 234, the detection system 130 indicates that the entity may not pass through the entry point (i.e., access is denied due to contamination).

In block 218, the decontamination system 132 overlays the reflected image of the entity in the smart mirror with one or more visualizations to represent corresponding locations of one or more different types of decontamination techniques. With embodiments, one or more decontamination techniques may be visualized. For example, the visualization over the hand may indicate sanitizer spray, while the visualization over a portion of the smart attire may indicate ultraviolet removal.

With embodiments, the visualizations for the contaminants (e.g., first visualizations) are different from the visualizations for the decontamination techniques (e.g., second visualizations).

In block 220, the decontamination system 132 determines whether the attempted decontamination count is less than a threshold. If the attempted decontamination count is less than a threshold, processing continues to block 222 (FIG. 2C), otherwise, processing continues to block 234. The attempted decontamination count indicates how many times decontamination has been attempted. After a certain number of attempts, the decontamination system 132 may determine that decontamination is not possible.

In block 222, the decontamination system 132 performs decontamination. In certain embodiments, the decontamination system 132 performs the decontamination in response to receiving input authorizing the decontamination. In block 224, the decontamination system 132 increments the attempted decontamination count.

At this point, the detection system 130 of the CPS system 120 receives control back from the decontamination system 132 of the CPS system 120. In block 226, the detection system 130 obtains updated sensor data and one or more updated images. In block 228, the detection system 130 detects any contaminants of the entity using any combination of the updated sensor data, the one or more updated images, and one or more contamination propagation patterns. In block 230, the detection system 130 determines whether the entity is contaminated. If so, processing continues to block 214 (FIG. 2B), otherwise, processing continues to block 232. In block 232, the detection system 130 indicates that the entity may pass through the entry point. Thus, in response to determining that the decontamination has been successful, the detection system 130 allows the entity to pass through the entry point.

That is, the decontamination is attempted, and then the detection system 130 determines again whether the entity is contaminated using the updated sensor data and images. The smart mirror 100 provides an intelligent access control system that would allow or deny entity movement based on detected contamination levels and any associated danger thereof.

In certain embodiments, the detection system 130 analyzes the degree of contamination and the spread of contamination on the user's smart attire. Then, based on the portions of the contamination on the smart attire, the decontamination system 132 proactively performs decontamination in addition to visually showing the decontamination progress in the user's reflection on the smart mirror 100 so that the user is able to visually see when the decontamination is completed.

For example, the smart mirror 100 may include a decontamination technique of spraying sanitizer to the contaminated portions, providing ultrasound decontamination, providing infrared decontamination, providing ultraviolet exposure for decontamination, etc. In addition, the smart mirror 100 may suggest a decontamination technique that the smart mirror 100 does not provide (e.g., washing hands).

In addition, based on the types of contamination and the contaminated portions on the smart attire, the detection system 130 provides appropriate visualization on the smart mirror 100 (e.g., color coding of different types of contaminants) so that user is able to see the criticality of the contamination and understand which portions should not be touched (to avoid the spread of contamination) before any decontamination is applied.

Moreover, depending on the type of detected contamination and the recommended decontamination technique, the decontamination system 132 may allow the user to approve the recommended actions. For example, the user may first approve ultrasound exposure using a hand gesture if the user is wearing Augmented Reality (AR) glasses.

Figure 3:
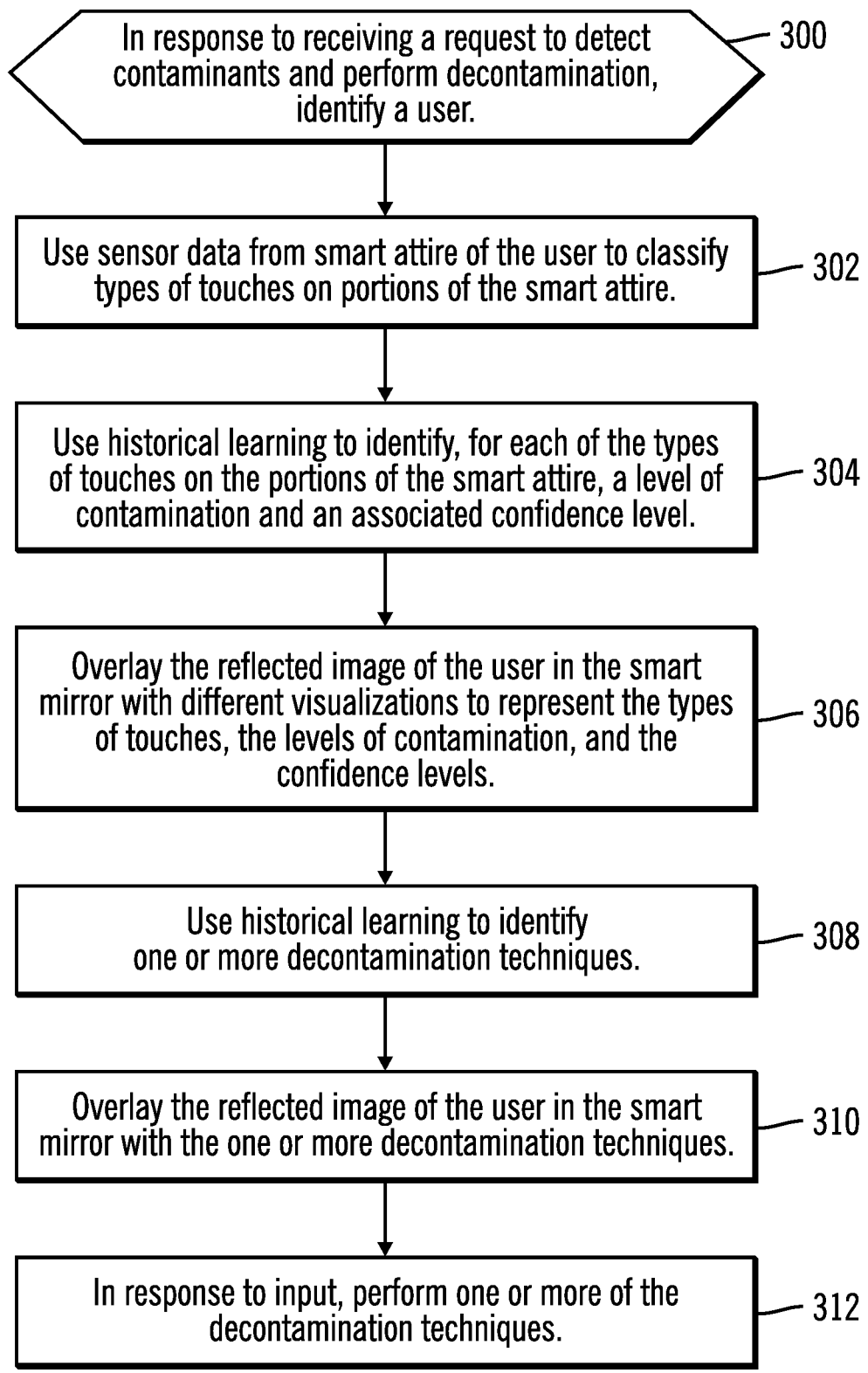
FIG. 3 illustrates, in a flowchart, operations for visualizing contaminants and decontamination techniques in accordance with certain embodiments.

FIG. 3 illustrates, in a flowchart, operations for visualizing contaminants and decontamination techniques in accordance with certain embodiments. In response to receiving a request to detect contaminants and perform decontamination, control begins at block 300 with the CPS system 120 identifying a user standing in front of the smart mirror, which is by an entry point.

In block 302, the CPS system 120 uses sensor data from smart attire of the user to classify types of touches on portions of the smart attire. In certain embodiments, the CPS system 120 uses sensor feed analysis from smart attire (e.g., a uniform of a doctor, a hospital gown of a patient, etc.) to classify different types of touches on any position of the smart attire, and the classifying of touches may be based on physical properties (e.g., solid versus liquid having different levels of viscosity, temperatures, etc.) and based on patterns of touch (e.g., rubbing, pressure, long duration touch, etc.).

In certain embodiments, based on the user performing any activity or spending time in any contaminated area, the CPS system 120 identifies various touch areas on the smart attire, hand, mouth, foot, etc., based on the duration of touch, properties of the contamination, and the area covered by the touch. The CPS system 120 determines the propagation of touch and the contamination propagation pattern on the user's body. For example, the user touches a contaminated area with a left hand and touches a portion of the smart attire with the left hand. This results in the portion becoming contaminated. Then the user touches the contaminated portion with a right hand, which results in the right hand becoming contaminated. In this case, the contamination propagation pattern is: left hand to portion to right hand.

In block 304, the CPS system 120 uses historical learning to identify, for each of the types of touches on the portions of the smart attire, a level of contamination and an associated confidence level. Historical learning may be described as learning new information based on new data and historical data (e.g., if a doctor enters a contaminated room of a hospital for 20 minutes, the doctor's smart attire is likely to become contaminated). In certain embodiments, the CPS system 120 recognizes different types of touches on the smart attire as having different levels of contamination (from no contamination to high contamination) and identifies an appropriate confidence level (e.g., 20% or 80% confidence level) for the contamination. For example, historical learning may indicate that touching an entity for 20 minutes is likely to result in high contamination with a confidence level of 75%. In certain embodiments, the CPS system 120 uses a machine learning model 140 for the operations of block 304.

In block 306, the CPS system 120 overlays the reflected image of the user in the smart mirror with different visualizations to represent the types of touches, the levels of contamination, and the confidence levels. In certain embodiments, the visualizations may be in different colors or may use different shapes to represent the types of touches, the levels of contamination, and the confidence levels. In certain embodiments, smart attire may be pared with the smart mirror 100 to overlay the classified touch pattern and confidence levels with different visualization on the reflected image. This is to represent different patterns of touches of the smart attire.

In block 308, the CPS system 120 uses historical learning to identify one or more decontamination techniques. In block 310, the CPS system 120 overlays the reflected image of the user in the smart mirror with the one or more decontamination techniques. In block 312, the CPS system 120, in response to input (e.g., from the user), performs one or more of the decontamination techniques. In certain embodiments, the CPS system 120 uses a machine learning model 140 for the operations of block 308.

In certain embodiments, the CPS system 120 recommends appropriate decontamination techniques, which are overlaid over the smart mirror, along with the visualizations, for the user to take action.

In certain embodiments, wearable devices, smart attire, or IoT enabled devices of any user or in the surrounding area of the user may be used by the CPS system 102 to predict whether the user is cross-contaminated based on the activity performed, time spent in that activity, surrounding environment, etc. The CPS system 120 may perform access control to ensure the user is decontaminated before moving through an entry point. This prevents the user from spreading contamination (e.g., outside of the contaminated area). For example, one medical worker spent time with a contaminated patient, so, based on the activity performed, time spent, etc., the CPS system 120 predicts whether the medical worker is also contaminated. With this example, before the medical worker passes through an entry point (e.g., coming out from an enclosed area), the CPS system 120 determines whether the medical worker has performed decontamination, and, if so, opens the entry point and, if not, closes (or locks) the entry point.

In certain embodiments, before allowing a user to pass through an entry point into or out of an area, the CPS system 120 obtains sensor data from the smart attire, sensor data about the user's activities, sensor data about time spent in different areas after a last decontamination, and data about the user's current health (e.g., from a user file) because the user's current health may spread contamination or may be impacted by contaminants. Using this information, the CPS system 120 predicts whether the user is contaminated. Based on the determination of contamination, the CPS system 120 performs access control to decide whether to allow the user to enter the area. For example, in a hospital, when a doctor is about to enter into a patient's room, the CPS system 120 determines whether the doctor is contaminated, and, based on this determination, determines whether to allow the doctor to enter the room. Also, the CPS system 120 may analyze the doctor's health condition for this determination (e.g., is the doctor is sneezing, which may make the patient further sick).

With embodiments, the IoT enabled CPS system 120 determines the contamination propagation pattern, and, based on a direction of propagation and an entity (that may carry and spread the contamination), the CPS system 120 takes proactive action so that contamination spread may be controlled (e.g., limited or prevented). For example, in an enclosed area, if the CPS system 120 detects that contamination may spread through air, the CPS system 120 may then automatically open or close windows and doors of the area so that contamination does not spread in the enclosed area.

In certain embodiments, based on historical data of contamination spreading in any area (e.g., based on a disease propagation pattern, pathology report, etc.), the CPS system 120 identifies the possible entry points of the contamination and recommends different types of decontamination techniques. For example, the CPS system 120 may identify the possible entry points and carriers of contamination, and recommend decontamination techniques to be applied (e.g., adding a carpet that emits ultrasound to kill germs at an entry point or installing decontamination systems in the window (e.g., sanitizing sprays)).

With embodiments, based on the predicted contamination propagation pattern, the severity of the contamination, and the type of contamination, the CPS system 120 dynamically auto-evolves the access control rules that are used to determine whether an entity may enter into an enclosed area or coming out from the enclosed area. For example, the CPS system 120 determines how the contamination is spreading based on the doctor's activity and updates the access control rules to enable to control the spread of contamination.

In certain embodiments, the historical learning captures types of touches on the smart attire, such as:
  touching a solid object (e.g., dry, solid, soft, hard, etc.)
  touching a liquid (e.g., level of viscosity, temperature, etc.)
  pattern of touching (e.g., moving hand over patient, pressing, duration of touch, etc.)
  area of user covered in the smart attire
  location where the objects are touched (e.g., while examining contaminated or non-contaminated patient in a hospital room, office area, etc.)
  doctors and pathological report around the touched areas
  usage feedback (e.g., the doctor nullifies any touch)

The historical data may be used for creating the knowledge corpus 190 to classify the types of touch.

In certain embodiments, the CPS system 120 incorporates user feedback into historical learning. For example, if the CPS system 120 determines that there has been a touch, the doctor may give feedback to the CPS system 120 that there was no touch. This feedback works in two ways: 1) the feedback allows user to override the CPS system 120 output/derivation/inference, and 2) the feedback allows the historical learning to improve in future through a reinforcement learning mechanism.

Figure 4:
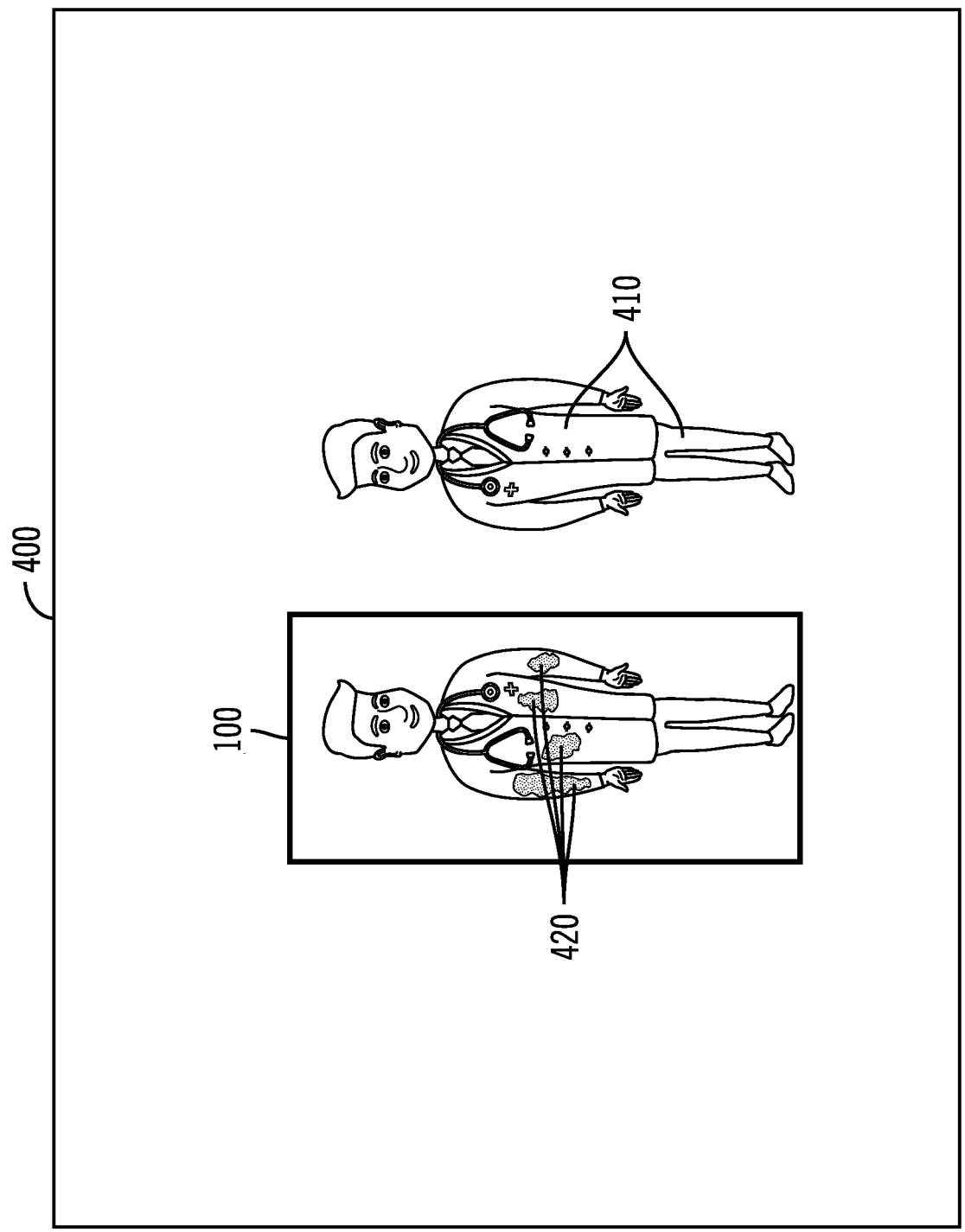
FIG. 4 illustrates a user in front of a smart mirror in accordance with certain embodiments.

FIG. 4 illustrates a user in front of a smart mirror in accordance with certain embodiments. In the example 400, a doctor wearing a uniform (smart attire with sensors 410) is standing in front of the smart mirror 100. The CPS system 120 identifies contaminated areas 420, highlights the contaminated areas (by overlaying the areas in the reflected image of the doctor), optionally indicates that decontamination is recommended, and identifies a decontamination technique (e.g., ultrasound exposure for 5 minutes). The CPS system 120 may implement the decontamination technique or the doctor may go elsewhere for decontamination and return to the smart mirror for the CPS system 120 to check for contamination again.

Figure 5:
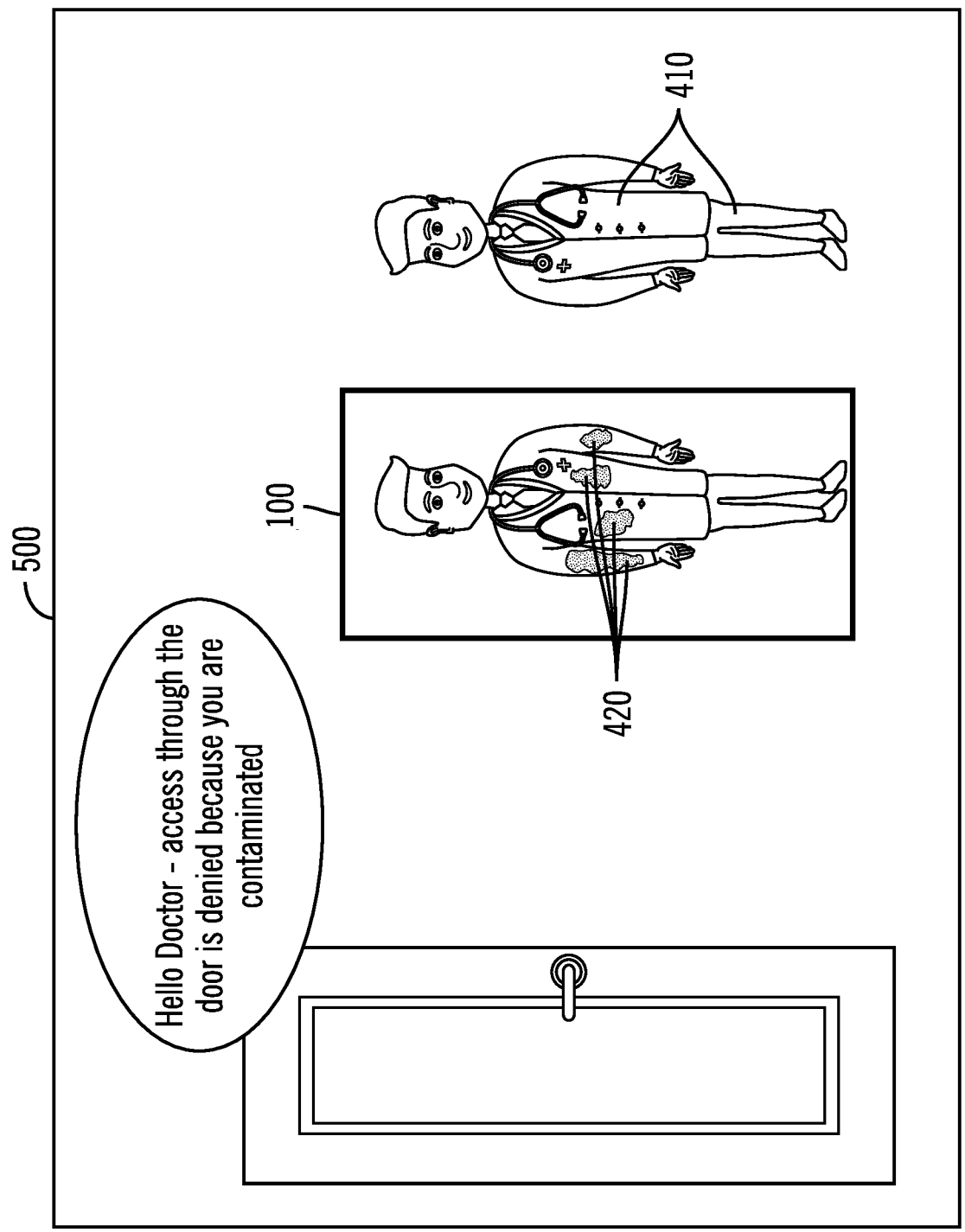
FIG. 5 illustrates access control in accordance with certain embodiments.

FIG. 5 illustrates access control in accordance with certain embodiments. In the example 500, the smart mirror 100 notifies the doctor that passage (entrance or exit) through the door (an example entry point) is denied because the doctor is contaminated.

In certain embodiments, an entity who is a user (e.g., a doctor) or an organization made up of entities (e.g., a hospital) actively sign up to allow the CPS system 120 to operate (e.g., sign up to allow the CPS system 120 to collect the sensor data, the images, and the contamination propagation patterns). Thus, with embodiments, the CPS system 120 does not collect sensor data or images unless authorized to do so.

With embodiments, the CPS system 120 identifies hand movements, touch activities, etc. based on visual processing (e.g., from the images taken by cameras), wearable devices (e.g., wearable devices worn by the medical workers or patients), and smart attire (e.g., a uniform or lab coat made with IoT enabled smart attire).

In certain embodiments, the CPS system 120 may use Region Based Convolutional Neural Networks (R-CNN) type of machine learning models for touch activity detection. In certain embodiments, the CPS system 120 may use K-Means clustering to differentiate between different types of users (e.g., the medical workers, patents, and visitors). In certain embodiments, the CPS system 120 may use different uniforms to identifies types of individuals (e.g., lab technicians versus doctors) or name tags to identify individuals (and then identify whether that individual is a lab technician or a doctor, etc., using information from a user file). In other embodiments, the CPS system 120 may use other techniques (e.g., a mobile phone or other unique identifier) to identify individuals.

In certain embodiments, the CPS system 120 analyzes medical data to identify the type of spreading of contamination (e.g., a disease already diagnosed or being diagnosed) and the contamination carrier (e.g., a doctor versus a patient).

In certain embodiments, the smart mirror 100 works with an IoT enabled zone that acts as a decontamination zone (e.g., in the case of a hospital, each patient room may be an IoT enabled zone). Thus, when an entity is leaving the IoT enabled zone, the smart mirror 100 is able to detect contamination and apply decontamination, if needed.

In certain embodiments, the CPS system 120 is an access control system that takes into consideration contamination and health parameters.

In certain embodiments, the CPS system 120 uses Artificial Intelligence (AI) techniques to determine the pattern of the contamination propagation. For example, the CPS system 120 may use supervised machine learning determine the pattern of the contamination propagation. As another example, the CPS system 120 may use real-time internet search and Natural Language Processing (NLP) to determine the pattern of the contamination propagation.

In certain embodiments, using IoT feed (i.e., sensor data) analysis, the learn the pattern of the contamination propagation identifies how the doctor and patients are interacting, and, based on the interaction pattern, the learn the pattern of the contamination propagation determines whether the doctors are contaminated.

In certain embodiments, the CPS system 120 analyzes the IoT feed to identify the types of interaction performed by the medical workers with other users or with objects (e.g., any medical equipment, etc.) and to identify how much time the doctor spent in the IoT enabled zone (e.g., patient's room).

In certain embodiments, the CPS system 120 identifies the contaminated areas based on touch using the IoT enabled zone and the smart attire of the user. The CPS system 120 also identifies contaminated or cross contaminated areas.

In certain embodiments, the CPS system 120 is an access control system that identifies each user individually and identifies the smart attire when identifying the contamination and cross-contamination patterns.

In certain embodiments, the CPS system 120 performs access control based on the types of contamination and the degree of contamination based on a security policy.

In certain embodiments, the CPS system 120 determines whether the decontamination was properly done. The CPS system 120 identifies the decontamination techniques and validates whether the decontamination techniques actually removed the contamination.

If the decontamination technique is properly done, then the CPS system 120 allows the user to come out from the IoT enabled zone. This is so that the user does not cause further cross contamination after coming out from the IoT enabled zone.

For any entry point, the CPS system 120 determines whether the user is contaminated and performs decontamination before allowing the user to pass through (i.e., enter or exit).

In certain embodiments, after decontamination techniques are applied, the detection system 130 of the CPS 120 may determine whether smart attire of a user is decontaminated and identify any areas of the smart attire that are still contaminated.

The smart mirror 100 may be used in any location that has one or more entry points. For example, the smart mirror 100 may be used at a hospital, a home, a restaurant, and a public area (e.g., a public building or a gated park). A user may be a doctor, medical workers, a patient, a visitor, a non-medical person, etc. For example, a user may have a smart mirror 100 at the entrance to a home, and the user may use the smart mirror to remove an contamination before entering the home. This safeguards the inside of the home and family members there.

In certain embodiments, user actively indicate whether or not they agree to have the smart mirror 100 collect sensor data and images of them. This may be done at the entrance to a location. For example, patients in a hospital may sign up for this to avoid the spread of contaminants.

With embodiments, the user may wear smart attires (which enables the CPS system 120 to identify touch points on the smart attire) and smart devices (which may identify hand movement, touch activity, etc.).

In certain embodiments, the CPS system 120 determines whether the user has touched objects or other users, how the user has touched them (e.g., holding an object or shaking hands with another user), whether the user has been to a location where contamination probability is high (e.g., a hospital or a busy road), how much time user has spent at various locations and with which other users, and what portions of the user's smart attire that the user has touched after touching an object or other user. These determinations may be made using R-CNN based activity detection and K-Means clustering.

In certain embodiments, the CPS system 120 recommends types of decontamination techniques to be applied (e.g., sanitizer spray, ultrasound, ultra violet exposure, washing, etc. These recommendations may be made based on supervised learning. For such supervised learning, he features may include User File, Type of Contamination, Level of Contamination, etc. Also, for such supervised learning, the labels may include: Recommendation Type (sanitizer spray, ultrasound, etc.) and Proposed Time (e.g., 1 minute for performing decontamination).

With embodiments, the CPS system 120 may perform the decontamination or the user may perform the decontamination manually. Then, the CPS system 120 provides decontamination results to the user. For example, the smart mirror 100 may indicate that the user has been decontaminated (e.g., with a visual clue reflected in the smart mirror (e.g., the reflection is shown in green), with a written message displayed in the smart mirror 100 (e.g., "you are good to go now"), or with the CPS system 120 verbally indicating this (e.g., "you may pass through the entry point").

In certain embodiments, the CPS system 120 may detect a pattern of a communicable disease (either air-borne or not air-borne) using social media, IoT devices, wearables, and smart attire. That is, in certain embodiments, the CPS system 120 collects information about diseases that are reported on social media (or otherwise on the internet) and how those diseases spread to determine contamination propagation patterns.

With embodiments, the CPS system 120 is able to control contamination propagation at entry points based on contamination propagation patterns. Different types of contamination may propagate in a different manner. The CPS system 120 is IoT and machine learning based to detect and highlight contaminated areas of body parts and smart attire in smart mirrors and to decontaminate the detected contaminated areas using the smart mirror 100. The CPS system 120 provides user access management based on dynamic detection of contamination level at entry points, where the user is restricted on contamination detection and allowed on decontamination. The CPS system 120 provides an intelligent access control system that allows/disallows people movement based on detected contamination levels and associated danger thereof.

Figure 6:
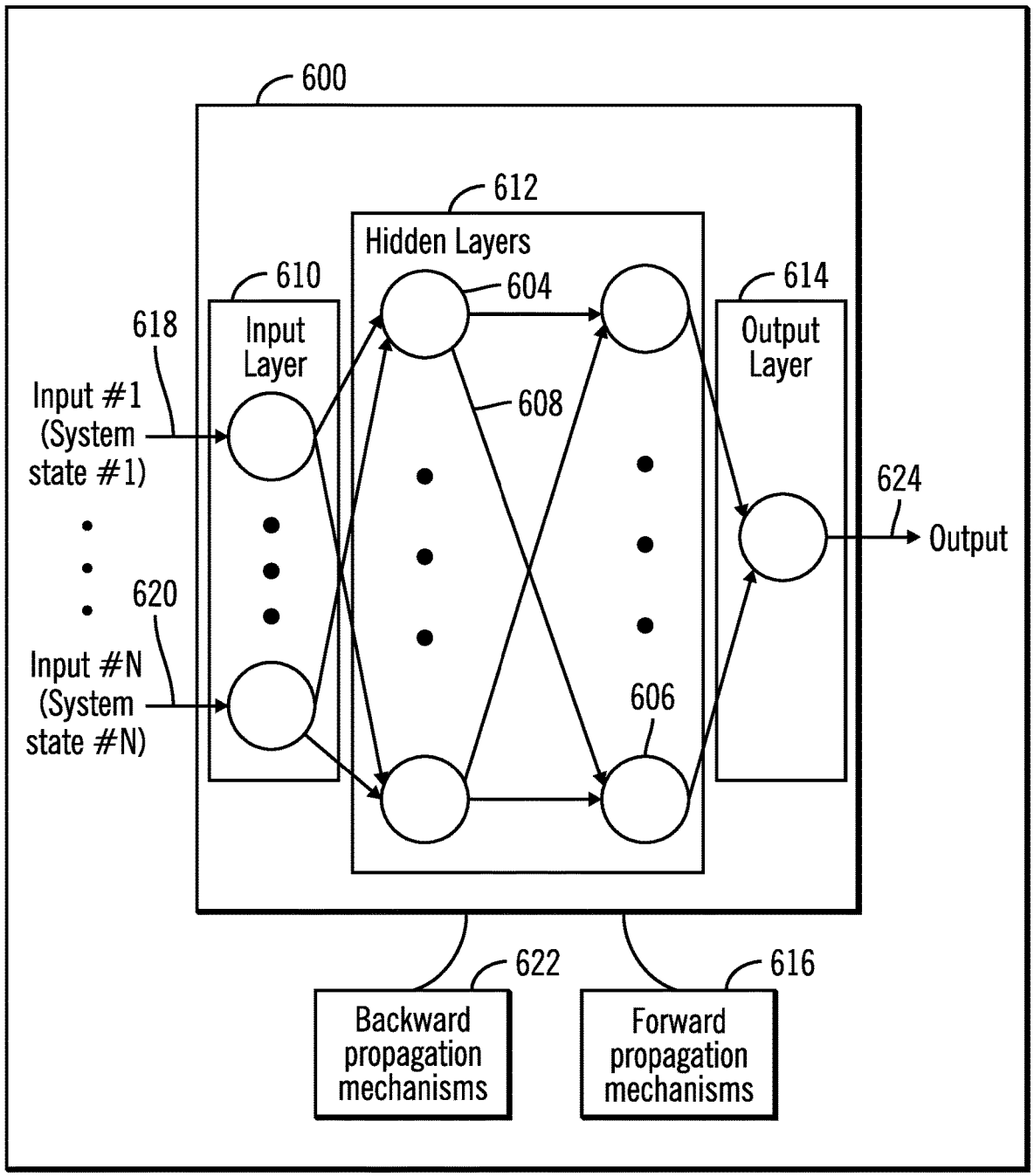
FIG. 6 illustrates, in a block diagram, details of a machine learning module in accordance with certain embodiments.

FIG. 6 illustrates, in a block diagram, details of a machine learning module 600 in accordance with certain embodiments. In certain embodiments, each of the one or more machine learning modules 140 are implemented using the components of the machine learning module 600.

The machine learning module 600 may comprise a neural network with a collection of nodes with links connecting them, where the links are referred to as connections. For example, FIG. 6 shows a node 604 connected by a connection 608 to the node 606. The collection of nodes may be organized into three main parts: an input layer 610, one or more hidden layers 612, and an output layer 614.

The connection between one node and another is represented by a number called a weight, where the weight may be either positive (if one node excites another) or negative (if one node suppresses or inhibits another). Training the machine learning module 600 entails calibrating the weights in the machine learning module 600 via mechanisms referred to as forward propagation 616 and backward propagation 622. Bias nodes that are not connected to any previous layer may also be maintained in the machine learning module 600. A bias may be described as an extra input of 1 with a weight attached to it for a node.

In forward propagation 616, a set of weights are applied to the input data 618 . . . 620 to calculate the output 624. For the first forward propagation, the set of weights may be selected randomly or set by, for example, a system administrator. That is, in the forward propagation 616, embodiments apply a set of weights to the input data 618 . . . 620 and calculate an output 624.

In backward propagation 622 a measurement is made for a margin of error of the output 624, and the weights are adjusted to decrease the error. Backward propagation 622 compares the output that the machine learning module 600 produces with the output that the machine learning module 600 was meant to produce, and uses the difference between them to modify the weights of the connections between the nodes of the machine learning module 600, starting from the output layer 614 through the hidden layers 612 to the input layer 610, i.e., going backward in the machine learning module 600. In time, backward propagation 622 causes the machine learning module 600 to learn, reducing the difference between actual and intended output to the point where the two come very close or coincide.

The machine learning module 600 may be trained using backward propagation to adjust weights at nodes in a hidden layer to produce adjusted output values based on the provided inputs 618 . . . 620. A margin of error may be determined with respect to the actual output 624 from the machine learning module 600 and an expected output to train the machine learning module 600 to produce the desired output value based on a calculated expected output. In backward propagation, the margin of error of the output may be measured and the weights at nodes in the hidden layers 612 may be adjusted accordingly to decrease the error.

Backward propagation may comprise a technique for supervised learning of artificial neural networks using gradient descent. Given an artificial neural network and an error function, the technique may calculate the gradient of the error function with respect to the artificial neural network's weights.

Thus, the machine learning module 600 is configured to repeat both forward and backward propagation until the weights of the machine learning module 600 are calibrated to accurately predict an output.

The machine learning module 600 implements a machine learning technique such as decision tree learning, association rule learning, artificial neural network, inductive programming logic, support vector machines, Bayesian models, etc., to determine the output value 624.

In certain machine learning module 600 implementations, weights in a hidden layer of nodes may be assigned to these inputs to indicate their predictive quality in relation to other of the inputs based on training to reach the output value 624.

With embodiments, the machine learning module 600 is a neural network, which may be described as a collection of "neurons" with "synapses" connecting them.

With embodiments, there may be multiple hidden layers 612, with the term "deep" learning implying multiple hidden layers. Hidden layers 612 may be useful when the neural network has to make sense of something complicated, contextual, or non-obvious, such as image recognition. The term "deep" learning comes from having many hidden layers. These layers are known as "hidden", since they are not visible as a network output.

In certain embodiments, training a neural network may be described as calibrating all of the "weights" by repeating the forward propagation 616 and the backward propagation 622.

In backward propagation 622, embodiments measure the margin of error of the output and adjust the weights accordingly to decrease the error.

Neural networks repeat both forward and backward propagation until the weights are calibrated to accurately predict the output 624.

In embodiments in which a machine learning module 140 is used by the detection system 130 to determine whether the entity is contaminated, the inputs are the sensor data, the one or more images, and the one or more contamination propagation patterns, while the outputs are the determination of whether there is contamination, along with the locations of different types and levels of contamination. In certain embodiments, the machine learning model 140 may be refined based on whether the outputs are indicated as accurate.

In certain embodiments, in which a machine learning module 140 is used by the detection system 130 to determine whether the entity is contaminated, the inputs are the types of touches on the portions of the smart attire, while the outputs are a level of contamination and an associated confidence level for each of the types of touches.

In embodiments in which another machine learning module 140 is used by the decontamination system 132 to select one or more decontamination techniques 134, the inputs are the sensor data, the one or more images, and the one or more contamination propagation patterns, while the outputs are zero or more decontamination techniques. In certain embodiments, the machine learning model 140 may be refined based on whether the outputs are indicated as accurate.

Figure 7:
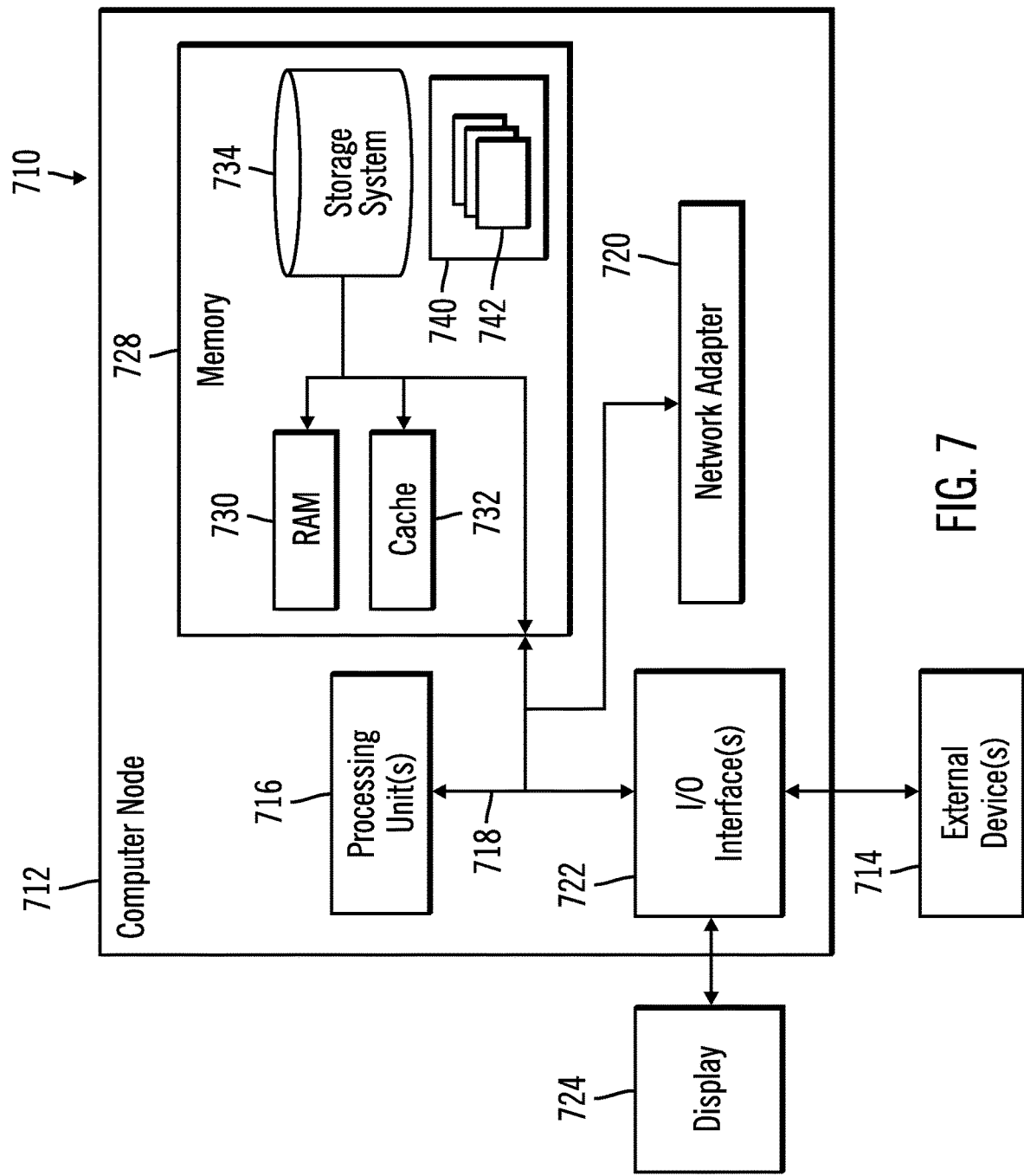
FIG. 7 illustrates a computing node in accordance with certain embodiments.

FIG. 7 illustrates a computing environment 710 in accordance with certain embodiments. In certain embodiments, the computing environment is a cloud computing environment. Referring to FIG. 7, computer node 712 is only one example of a suitable computing node and is not intended to suggest any limitation as to the scope of use or functionality of embodiments of the invention described herein. Regardless, computer node 712 is capable of being implemented and/or performing any of the functionality set forth hereinabove.

The computer node 712 may be a computer system, which is operational with numerous other general purpose or special purpose computing system environments or configurations. Examples of well-known computing systems, environments, and/or configurations that may be suitable for use with computer node 712 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer node 712 may be described in the general context of computer system executable instructions, such as program modules, being executed by a computer system. Generally, program modules may include routines, programs, objects, components, logic, data structures, and so on that perform particular tasks or implement particular abstract data types. Computer node 712 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer node 712 is shown in the form of a general-purpose computing device. The components of computer node 712 may include, but are not limited to, one or more processors or processing units 716, a system memory 728, and a bus 718 that couples various system components including system memory 728 to one or more processors or processing units 716.

Bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer node 712 typically includes a variety of computer system readable media. Such media may be any available media that is accessible by computer node 712, and it includes both volatile and non-volatile media, removable and non-removable media.

System memory 728 can include computer system readable media in the form of volatile memory, such as random access memory (RAM) 730 and/or cache memory 732. Computer node 712 may further include other removable/non-removable, volatile/non-volatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a compact disc read-only memory (CD-ROM), digital versatile disk read-only memory (DVD-ROM) or other optical media can be provided. In such instances, each can be connected to bus 718 by one or more data media interfaces. As will be further depicted and described below, system memory 728 may include at least one program product having a set (e.g., at least one) of program modules that are configured to carry out the functions of embodiments of the invention.

Program/utility 740, having a set (at least one) of program modules 742, may be stored in system memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer node 712 may also communicate with one or more external devices 714 such as a keyboard, a pointing device, a display 724, etc.; one or more devices that enable a user to interact with computer node 712; and/or any devices (e.g., network card, modem, etc.) that enable computer node 712 to communicate with one or more other computing devices. Such communication can occur via Input/Output (I/O) interfaces 722. Still yet, computer node 712 can communicate with one or more networks such as a local area network (LAN), a general wide area network (WAN), and/or a public network (e.g., the Internet) via network adapter 720. As depicted, network adapter 720 communicates with the other components of computer node 712 via bus 718. It should be understood that although not shown, other hardware and/or software components could be used in conjunction with computer node 712. Examples, include, but are not limited to: microcode, device drivers, redundant processing units, external disk drive arrays, Redundant Array of Inexpensive Disks (RAID) systems, tape drives, and data archival storage systems, etc.

In certain embodiments, the smart mirror 100 includes a computing device with the architecture of computer node 710. In certain embodiments, the smart mirror 100 and/or the data store 150 are part of a cloud infrastructure. In certain alternative embodiments, the smart mirror 100 and/or the data store 150 are not part of a cloud infrastructure.

Cloud Embodiments

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
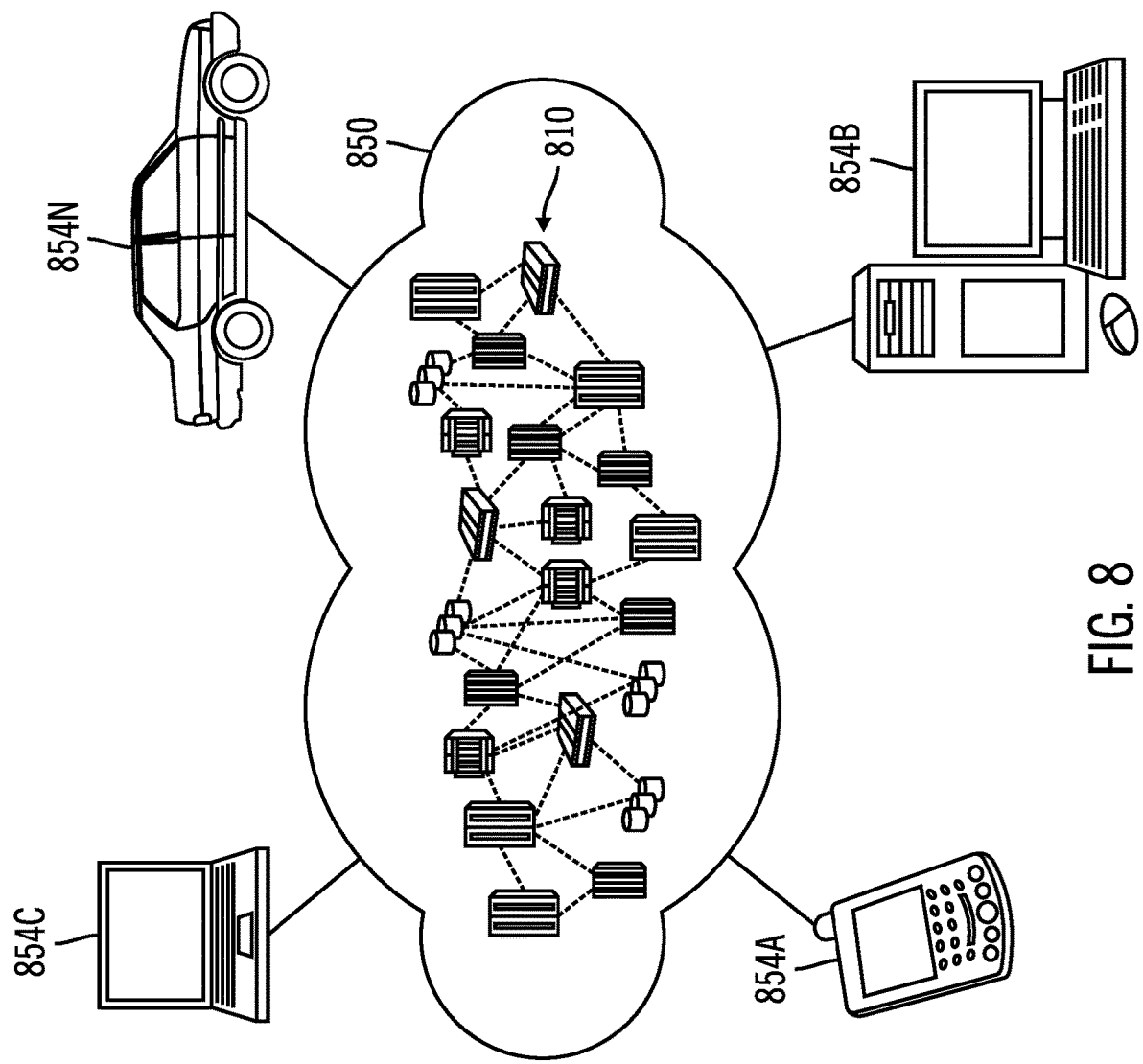
FIG. 8 illustrates a cloud computing environment in accordance with certain embodiments.

Referring now to FIG. 8, illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Nodes 810 may communicate with one another. They may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
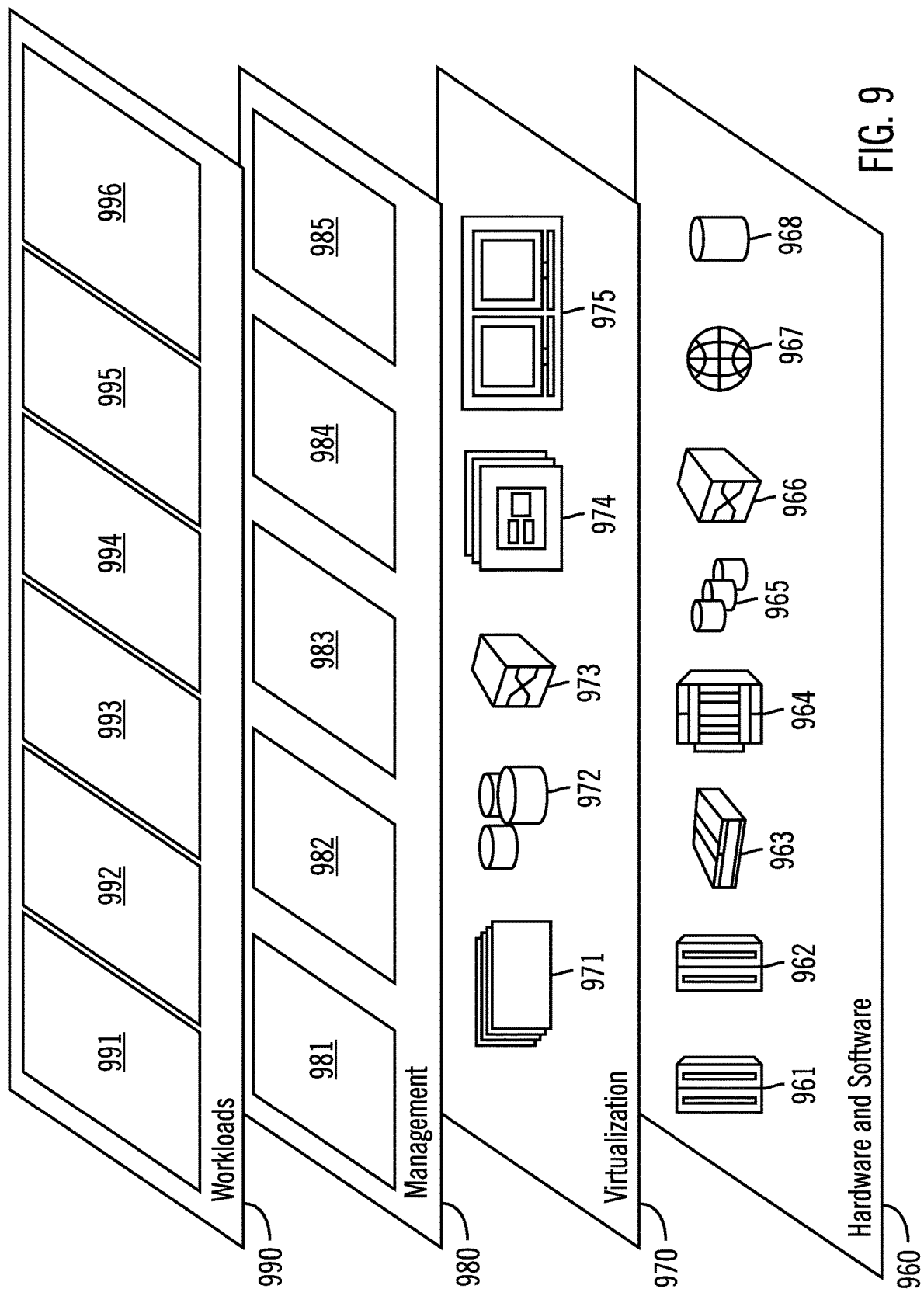
FIG. 9 illustrates abstraction model layers in accordance with certain embodiments.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 includes hardware and software components. Examples of hardware components include: mainframes 961; RISC (Reduced Instruction Set Computer) architecture based servers 962; servers 963; blade servers 964; storage devices 965; and networks and networking components 966. In some embodiments, software components include network application server software 967 and database software 968.

Virtualization layer 970 provides an abstraction layer from which the following examples of virtual entities may be provided: virtual servers 971; virtual storage 972; virtual networks 973, including virtual private networks; virtual applications and operating systems 974; and virtual clients 975.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Examples of workloads and functions which may be provided from this layer include: mapping and navigation 991; software development and lifecycle management 992; virtual classroom education delivery 993; data analytics processing 994; transaction processing 995; and detecting contamination propagation and performing decontamination using a smart mirror 996.

Thus, in certain embodiments, software or a program, implementing detecting contamination propagation and performing decontamination using a smart mirror in accordance with embodiments described herein, is provided as a service in a cloud environment. In certain embodiments, the operations to detect contamination and identify one or more decontamination techniques may be performed at a computing node in the cloud infrastructure, while the CPS system 120 executes the one or more decontamination techniques and/or determines access through an entry point based on whether the computing node indicates that the decontamination was successful.

Additional Embodiment Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, embodiments of the invention reside in the claims herein after appended. The foregoing description provides examples of embodiments of the invention, and variations and substitutions may be made in other embodiments.

What is claimed is:

1. A computer-implemented method, comprising operations for:
    in response to receiving a request to detect contaminants and perform decontamination, identifying an entity;
    detecting whether there are contaminants on the entity using any combination of sensor data, one or more images, and one or more contamination propagation patterns;
    in response to determining that there are no contaminants, allowing the entity to pass through an entry point; and
    in response to determining that there are contaminants,
        identifying one or more decontamination techniques;
        performing decontamination of the entity using the one or more decontamination techniques; and
        in response to determining that the decontamination has been successful, allowing the entity to pass through the entry point.

2. The computer-implemented method of claim 1, further comprising operations for:
    identifying and storing one or more new contamination propagation patterns of the entity.

3. The computer-implemented method of claim 1, further comprising operations for:
    overlaying a reflected image of the entity in a smart mirror with one or more visualizations to represent corresponding one or more locations of different types and levels of contamination.

4. The computer-implemented method of claim 1, further comprising operations for:
    overlaying a reflected image of the entity in a smart mirror with one or more visualizations to represent corresponding locations of one or more different types of decontamination techniques.

5. The computer-implemented method of claim 1, further comprising operations for:
    determining whether an attempted decontamination count is less than a threshold, wherein the decontamination is performed when the decontamination count is less than the threshold, and wherein the entity is denied passage through the entry point when the decontamination count is equal to or more than the threshold.

6. The computer-implemented method of claim 1, further comprising operations for:
    using the sensor data from smart attire of the entity to classify types of touches on portions of the smart attire; and
    using historical learning to identify, for each of the types of touches on the portions of the smart attire, a level of contamination and an associated confidence level.

7. The computer-implemented method of claim 1, wherein a Software as a Service (SaaS) is configured to perform the operations of the computer-implemented method.

8. A computer program product, the computer program product comprising a non-transitory computer readable storage medium having program code embodied therewith, the program code executable by at least one processor to perform operations for:
    in response to receiving a request to detect contaminants and perform decontamination, identifying an entity;
    detecting whether there are contaminants on the entity using any combination of sensor data, one or more images, and one or more contamination propagation patterns;
    in response to determining that there are no contaminants, allowing the entity to pass through an entry point; and
    in response to determining that there are contaminants,
        identifying one or more decontamination techniques;
        performing decontamination of the entity using the one or more decontamination techniques; and
        in response to determining that the decontamination has been successful, allowing the entity to pass through the entry point.

9. The computer program product of claim 8, wherein the program code is executable by the at least one processor to perform operations for:
    identifying and storing one or more new contamination propagation patterns of the entity.

10. The computer program product of claim 8, wherein the program code is executable by the at least one processor to perform operations for:
    overlaying a reflected image of the entity in a smart mirror with one or more visualizations to represent corresponding one or more locations of different types and levels of contamination.

11. The computer program product of claim 8, wherein the program code is executable by the at least one processor to perform operations for:
    overlaying a reflected image of the entity in a smart mirror with one or more visualizations to represent corresponding locations of one or more different types of decontamination techniques.

12. The computer program product of claim 8, wherein the program code is executable by the at least one processor to perform operations for:
    determining whether an attempted decontamination count is less than a threshold, wherein the decontamination is performed when the decontamination count is less than the threshold, and wherein the entity is denied passage through the entry point when the decontamination count is equal to or more than the threshold.

13. The computer program product of claim 8, wherein the program code is executable by the at least one processor to perform operations for:
   using the sensor data from smart attire of the entity to classify types of touches on portions of the smart attire; and
   using historical learning to identify, for each of the types of touches on the portions of the smart attire, a level of contamination and an associated confidence level.

14. The computer program product of claim 8, wherein a Software as a Service (SaaS) is configured to perform the operations of the computer program product.

15. A computer system, comprising:
   one or more processors, one or more computer-readable memories and one or more computer-readable, tangible storage devices; and
   program instructions, stored on at least one of the one or more computer-readable, tangible storage devices for execution by at least one of the one or more processors via at least one of the one or more computer-readable memories, to perform operations comprising:
   in response to receiving a request to detect contaminants and perform decontamination, identifying an entity;
   detecting whether there are contaminants on the entity using any combination of sensor data, one or more images, and one or more contamination propagation patterns;
   in response to determining that there are no contaminants, allowing the entity to pass through an entry point; and
   in response to determining that there are contaminants, identifying one or more decontamination techniques;
   performing decontamination of the entity using the one or more decontamination techniques; and
   in response to determining that the decontamination has been successful, allowing the entity to pass through the entry point.

16. The computer system of claim 15, wherein the operations further comprise:
   identifying and storing one or more new contamination propagation patterns of the entity.

17. The computer system of claim 15, wherein the operations further comprise:
   overlaying a reflected image of the entity in a smart mirror with one or more visualizations to represent corresponding one or more locations of different types and levels of contamination.

18. The computer system of claim 15, wherein the operations further comprise:
   overlaying a reflected image of the entity in a smart mirror with one or more visualizations to represent corresponding locations of one or more different types of decontamination techniques.

19. The computer system of claim 15, wherein the operations further comprise:
   determining whether an attempted decontamination count is less than a threshold, wherein the decontamination is performed when the decontamination count is less than the threshold, and wherein the entity is denied passage through the entry point when the decontamination count is equal to or more than the threshold.

20. The computer system of claim 15, wherein a Software as a Service (SaaS) is configured to perform the operations of the computer system.

* * * * *